(12) United States Patent
Rao et al.

(10) Patent No.: US 12,050,179 B2
(45) Date of Patent: Jul. 30, 2024

(54) METHOD FOR EXTRACTING RAMAN CHARACTERISTIC PEAKS EMPLOYING IMPROVED PRINCIPAL COMPONENT ANALYSIS

(71) Applicant: ZHEJIANG UNIVERSITY, Zhejiang (CN)

(72) Inventors: Xiuqin Rao, Zhejiang (CN); Yanning Zhang, Zhejiang (CN); Xiaomin Zhang, Zhejiang (CN); Yitian Wang, Zhejiang (CN); Yangyang Lin, Zhejiang (CN); Yibin Ying, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 260 days.

(21) Appl. No.: 17/765,846

(22) PCT Filed: Jun. 12, 2020

(86) PCT No.: PCT/CN2020/095775
§ 371 (c)(1),
(2) Date: Apr. 1, 2022

(87) PCT Pub. No.: WO2021/068545
PCT Pub. Date: Apr. 15, 2021

(65) Prior Publication Data
US 2022/0390374 A1    Dec. 8, 2022

(30) Foreign Application Priority Data

Oct. 8, 2019   (CN) .......................... 201910949963.9

(51) Int. Cl.
G01N 21/65   (2006.01)
G01N 33/12   (2006.01)

(52) U.S. Cl.
CPC ............. *G01N 21/65* (2013.01); *G01N 33/12* (2013.01)

(58) Field of Classification Search
CPC . G01N 21/65; G01N 33/12; G01N 2201/1293
See application file for complete search history.

(56) References Cited

U.S. PATENT DOCUMENTS

2008/0201093 A1 * 8/2008 Anderssen ......... G01N 21/3563
702/81

FOREIGN PATENT DOCUMENTS

| CN | 105424675 | 3/2016 |
| CN | 107044967 | 8/2017 |

(Continued)

OTHER PUBLICATIONS

De Biasio (Jun. 2015, Micro-Raman spectroscopy for meat type detection. In Next-Generation Spectroscopic Technologies VIII (vol. 9482, pp. 377-382 (Year: 2015).*

(Continued)

*Primary Examiner* — Edmond C Lau
*Assistant Examiner* — Mohamed Doumbia
(74) *Attorney, Agent, or Firm* — JCIPRNET

(57) ABSTRACT

A method for extracting Raman characteristic peaks employing improved principal component analysis comprising: using a confocal microscopic Raman-spectroscopic instrument to collect Raman spectroscopic data from surfaces of pork and beef samples; and performing preprocessing on the Raman spectroscopic data, performing principal component analysis, establishing a principal component loading scatter plot, extracting dot characteristics from the principal component loading scatter plot, analyzing same, and performing filtering on the dot characteristics to obtain Raman characteristic peaks. The method for extracting Raman characteristic peaks employing improved principal component analy- (Continued)

sis is used to extract Raman characteristic peaks from pork and beef samples, and then the Raman characteristic peaks are inputted into a classifier to undergo classification, thereby achieving high accuracy and quick classification.

4 Claims, 4 Drawing Sheets

(56) References Cited

FOREIGN PATENT DOCUMENTS

| CN | 109060709 | 12/2018 |
|---|---|---|
| CN | 110132938 | 8/2019 |
| CN | 110672582 | 1/2020 |

OTHER PUBLICATIONS

Boyaci (2014. A novel method for discrimination of beef and horsemeat using Raman spectroscopy. Food chemistry, 148, pp. 37-41) (Year: 2014).*

De Biasio (Jun. 2015, Micro-Raman spectroscopy for meat type detection. In Next-Generation Spectroscopic Technologies VIII (vol. 9482, pp. 377-382) (Year: 2018).*

Boyac (2014. A novel method for discrimination of beef and horsemeat using Raman spectroscopy. Food chemistry, 148, pp. 37-41) (Year: 2014).*

I. H. Boyaci et al., "A rapid method for determination of the origin of meat and meat products based on the extracted fat spectra by using of Raman spectroscopy and chemometric method," European Food Research and Technology, Jan. 2014, pp. 845-852.

G. Reich, "Recognizing chromatographic peaks with pattern recognition methods : Part 1. Development of a k-nearest-neighbour technique," Analytica Chimica Acta, May 1987, pp. 153-170.

Peng Zhang et al., "Peak detection using peak tree approach for mass spectrometry data," International Journal of Hybrid Intelligent Systems, Dec. 2008, pp. 197-208.

Tu Bin et al., "Research on detection method of peanut oil adulteration based on data fusion technology of multi-source spectral characteristics," Food and Fermentation Industries, vol. 42, Apr. 2016, pp. 169-173.

"International Search Report (Form PCT/ISA/210) of PCT/CN2020/095775", mailed on Aug. 28, 2020, with English translation thereof, pp. 1-6.

* cited by examiner

METHOD FOR EXTRACTING RAMAN CHARACTERISTIC PEAKS EMPLOYING IMPROVED PRINCIPAL COMPONENT ANALYSIS

CROSS-REFERENCE TO RELATED APPLICATION

This application is a 371 of international application of PCT application serial no. PCT/CN2020/095775, filed on Jun. 12, 2020, which claims the priority benefit of China application no. 201910949963.9, filed on Oct. 8, 2019. The entirety of each of the above mentioned patent applications is hereby incorporated by reference herein and made a part of this specification.

TECHNICAL FIELD

The disclosure relates to a method for extracting spectral characteristics of biological tissues, and particularly relates to a method for extracting Raman characteristic peaks employing improved principal component analysis.

DESCRIPTION OF RELATED ART

Raman spectroscopy is a spectral analysis technology based on the Raman scattering effect, has advantages such as strong spectral interpretation, rich information, and simple preprocessing, and is widely used in aspects such as materials, biology, and food safety. Each specific functional group or group in a Raman spectrum generates different characteristic peaks due to different vibrational structures. For a substance with complex compound composition, the Raman spectral signal consists of multiple peaks. When performing quantitative and qualitative analyses on the spectrum, accurately extracting the Raman characteristic peaks of a sample can reduce the complexity of the model and improve the generalization performance of the model. Reich G. et al. (Reich G. Recognizing chromatographic peaks with pattern recognition methods Part 1. Development of a k-nearest-neighbor technique[J]. Analytica Chimica Acta, 1987, 201: 153-170) proposed to use a KNN method to extract characteristic peaks, which adopted a sliding average window to sequentially compare Raman spectral signals of samples with a standard signal to identify the peaks. Zhang et al. (Zhang P, Li H, Zhou X, et al. Peak detection using peak tree approach for mass spectrometry data[J]. International Journal of Hybrid Intelligent Systems, 2008, 5(4):197-208) adopted a method for detecting characteristic peaks based on a peak tree, which had a good effect on positioning sparse peaks. Tu Bin et al. (Tu Bin[1], Chen Zhi[1], Bloomberg [1], et al. Detection of adulteration of peanut oil based on multi-source spectral feature fusion technology [J]. Food and Fermentation Industries, 2016, 42(4):169-173), which adopted a method for extracting characteristic peaks based on a backward interval partial least squares method to detect adulteration of peanut oil, and a total of 416 characteristic wavelengths were extracted.

Meat samples with complex components contain various groups, and the peaks overlap with one another. Therefore, the methods proposed by Reich G and Zhang et al. are often difficult to identify the characteristic peaks of the samples in meat classification. However, there are too many characteristic vectors filtered by the backward interval partial least squares method, which increases the complexity of the model. Therefore, it is necessary to select an appropriate method for extracting Raman characteristic peaks to improve the robustness and the processing speed of a model.

SUMMARY

Aiming at the shortcomings of low robustness or too many characteristics and complex models in the previous methods for extracting characteristics, the disclosure proposes a method for extracting Raman characteristic peaks employing improved principal component analysis.

As shown in FIG. 1, the technical schemes adopted by the disclosure to solve the technical problems are as follows.

1) A confocal microscopic Raman-spectroscopic instrument is used to collect Raman spectroscopic data from surfaces of pork and beef samples.

2) Preprocessing is performed on the Raman spectroscopic data, principal component analysis is then performed, a principal component loading scatter plot is then established, scatter characteristics of the principal component loading scatter plot are then analyzed and extracted, and the Raman characteristic peaks are filtered according to the scatter characteristics.

The scatter characteristics are the polar diameter and the polar angle of the scatter.

The preprocessing includes sequentially performing smoothing and baseline correction processing.

The key processing of the disclosure is to create the principal component loading scatter plot, and extract the Raman characteristic peaks according to the scatter characteristics. The following uses the principal component loading scatter plot to further optimize the result of the principal component analysis, and extract and classify the Raman characteristic peaks.

Step 2) specifically includes the following.

2.1) For a Raman spectrum dataset $B(B_1, B_2, \ldots, B_n)$ of n samples and m wave bands obtained after the preprocessing, that is, each spectrum $B_i$ contains m wave bands, a random sampling method is adopted to extract ⅔ spectrum from the dataset B to form a training set $C(C_1, C_2, \ldots, C_{2n/3})$. Then, principal component analysis is performed on the training set C to extract first two principal components $PC_1$ and $PC_2$, which are expressed as:

$$PC_1 = \sum_{k=1}^{m} \alpha_{1k} \beta_k$$

$$PC_2 = \sum_{k=1}^{m} \alpha_{2k} \beta_k$$

where $\beta_k$ is a k-th wave band, $\alpha_{1k}$ represents a load factor corresponding to the k-th wave band under the first principal component, and $\alpha_{2k}$ represents a load factor corresponding to the k-th wave band under the second principal component.

2.2) Draw a Load Distribution Diagram in the Form of Polar Coordinates

A two-dimensional coordinate graph is established with a load coefficient $\alpha_{1k}$ as the horizontal axis and a load coefficient $\alpha_{2k}$ as the vertical axis. The load coefficient $\alpha_{1k}$ and the load coefficient $\alpha_{2k}$ corresponding to a Raman shift point $\beta_k$ of the same wave band in the two principal components are taken as scatter coordinates $(\alpha_{1k}, \alpha_{2k})$, which are drawn in the two-dimensional coordinate graph to form a principal component loading scatter plot, that is, to draw a scatter plot of the load coefficient $\alpha_{jk}$ of each Raman shift point $\beta_k$, where j=1 or 2. Then, the scatters are converted from Cartesian coordinates ($\alpha_{1k}$, $\alpha_{2k}$) into polar coordinates ($d_k$, $\theta_k$). A wavelength range occupied by all scatters is divided into eight regions $D_i$(i=1, 2, ..., 8) according to angles of the polar coordinates, which are respectively $$\left[0, \frac{\pi}{4}\right), \left[\frac{\pi}{4}, \frac{\pi}{2}\right), \left[\frac{\pi}{2}, \frac{3\pi}{4}\right), \left[\frac{3\pi}{4}, \pi\right), \left[\pi, \frac{5\pi}{4}\right), \left[\frac{5\pi}{4}, \frac{3\pi}{2}\right), \left[\frac{3\pi}{2}, \frac{7\pi}{4}\right), \left[\frac{7\pi}{4}, 2\pi\right).$$

2.3) Determination of Positions of Characteristic Peaks

For each region $D_i$, a weighted distance $d_{ik}$ of each scatter ($\alpha_{1k}$, $\alpha_{2k}$) from the coordinate center is calculated.

$$d_{ik} = \frac{\sqrt{(\lambda_1 \alpha_{1k})^2 + (\lambda_2 \alpha_{2k})^2}}{\sqrt{\lambda_1^2 + \lambda_2^2}}$$

where $\lambda_1$ and $\lambda_2$ respectively represent weights of the first principal component and the second principal component, and $d_{ik}$ represents a weighted distance of a scatter corresponding to the k-th wave band of the i-th region $D_i$.

A variance $v_i$ and a mean $e_i$ of the weighted distances $d_{ik}$ of all scattered points in each region are calculated. The maximum weighted distance $d_{ik}$ is taken as the maximum polar diameter $r_i$ to perform the following judgment.

For each maximum polar diameter $r_i$, if $$\frac{r_i - e_i}{v_i} \geq 3$$

is satisfied, the Raman shift point $\beta_k$ corresponding to the maximum polar diameter $r_i$ is regarded as a Raman characteristic peak.

Dividing the wavelength range occupied by all scatters into eight regions according to the angles of the polar coordinates specifically includes dividing the principal component loading scatter plot into eight sector-shaped regions according to the angles with the coordinate center of the plot as an origin.

In the specific implementation, a method for inputting the Raman characteristic peaks into a k-nearest neighbor classification model for training may be further adopted to classify the meat samples to implement the identification of the meat samples, which may be used to implement the identification of beef samples mixed with pork and may also be used to identify whether a meat sample is a beef sample or a pork sample.

The disclosure uses a confocal microscopic Raman spectroscopic instrument to respectively collect raw data from the surfaces of the beef and pork samples, and may perform preprocessing of denoising and baseline correction on the spectroscopic data by a chemometric method. Then, principal component analysis is performed on the corrected spectrum to create the principal component loading scatter plot. The distribution characteristics of the scatter plot are obtained by analysis. The Raman characteristic peaks are extracted.

The beneficial effects that the disclosure has are as follows.

Aiming at the characteristics of the Raman peaks of pork and beef, the disclosure improves the method for extracting Raman characteristic peaks employing principal component analysis. The extracted Raman characteristic peaks are used for high accuracy classification and quick classification. The Raman characteristic peaks of beef and pork may be extracted by the method of the disclosure and substituted into a classifier for classification, thereby achieving high accuracy.

DETAILED DESCRIPTION OF DISCLOSED EMBODIMENTS

The disclosure will be further described below with reference to the drawings and embodiments.

Figure 1:
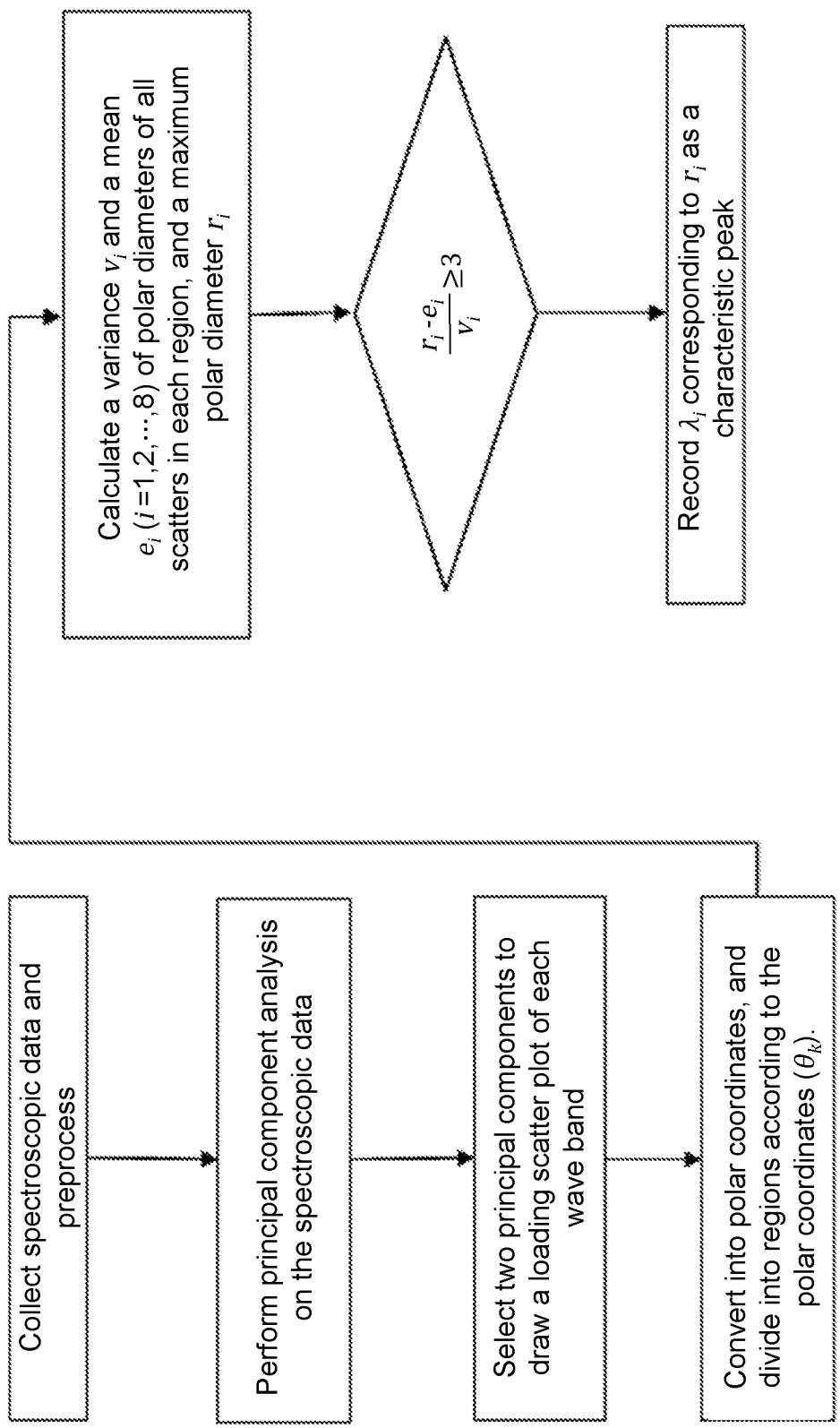
FIG. 1 is flowchart of processing of Raman spectrum data according to the disclosure.
Figure 2:
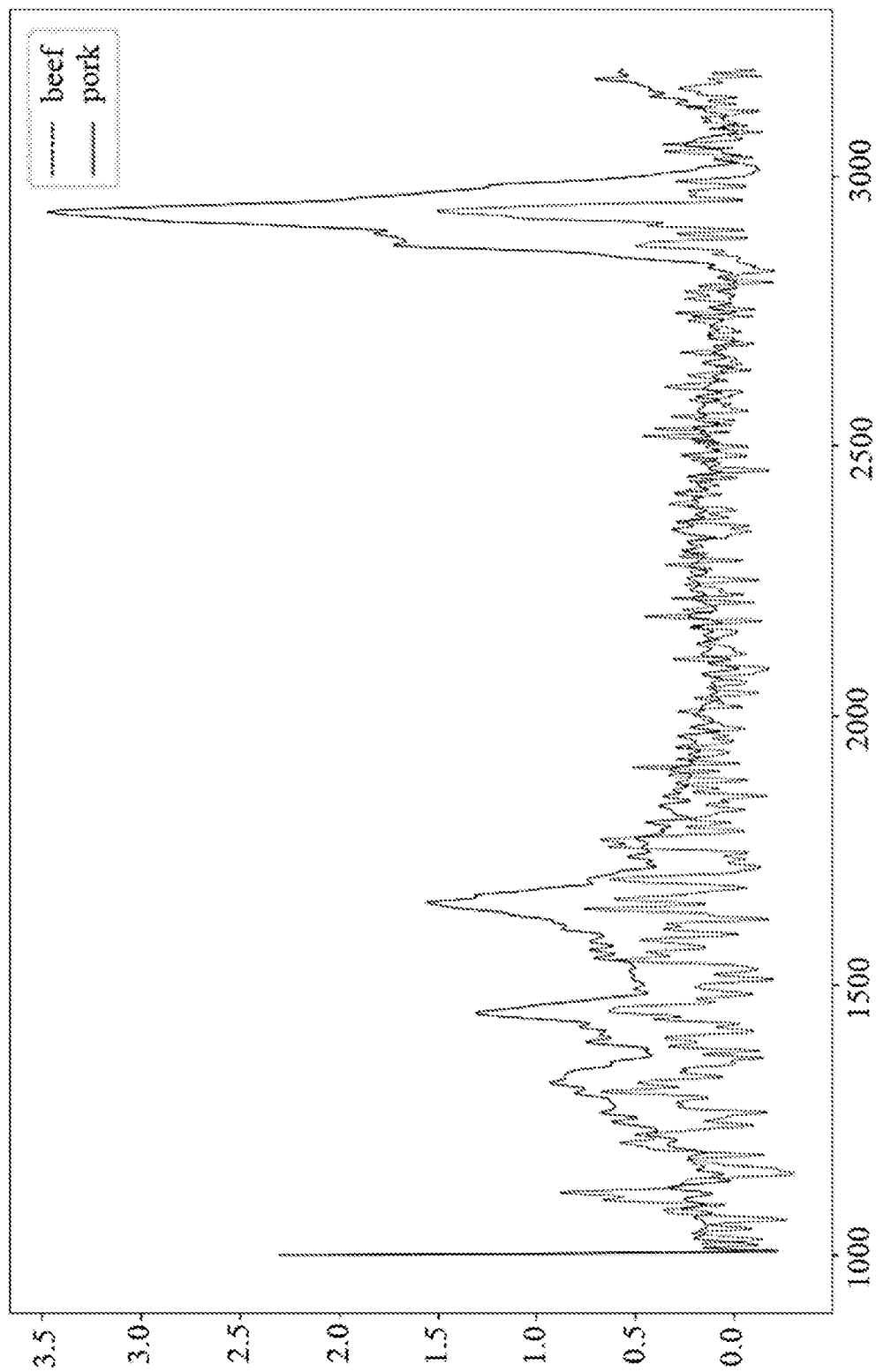
FIG. 2 are original peak graphs of pork and beef according to the disclosure.

As shown in FIG. 1, an embodiment of the disclosure and the implementation process are as follows.

In the example, mainly three types of samples were distinguished, which were respectively an equally mixed adulterated minced meat sample and minced meat samples of pure beef and pure pork. The meat sources were all vacuum-packed fresh pork and beef tenderloin slaughtered in the same batch (slaughtered and processed according to the standard and passed the inspection of the health and quarantine department, and after 24 hours of acid removal). Before the experiment, the meat was removed from the freezer, thawed in room temperature water, and then air-dried to remove obvious fats and connective tissues in the sample. Pork and beef were equally mixed and placed into the meat grinder and stirred twice for 30 s each time to obtain the adulterated minced meat sample. Then, pure beef and pure pork were respectively placed into the meat grinder and stirred twice for 30 s each time to obtain the pure beef minced meat sample and the pure pork minced meat sample.

The following are the collection of Raman spectra of pork and beef, the extraction of characteristic peaks, and the method for establishing models based on the same.

A) Collection of Raman spectra of samples. In the example, a Raman spectrometer (Raman spectrometer-LabRAM HR evolution) with 633 nm excitation light source was selected as the collection instrument. The cooling temperature of the CCD camera was −65° C., and the exposure time was 3 s. The effective power of the line laser light source was 25%. After data of the three types of samples were collected, the data was exported to txt format and transmitted to a PC. In the example, 30 spectra of the beef minced meat, the pork minced meat, and the adulterated minced meat samples were collected. The Raman spectra of the beef, the pork, and the adulterated minced meat samples were respectively denoted as $B_i$, $P_i$, and $M_i$(i=1, 2, ..., 30).

B) Smoothing and denoising of Raman spectra. The window size m=21 over which smoothed data was established was specified for each spectrum. For the center point of the window, a fifth-order polynomial was used to fit data points in the window to form a system of equations composed of 21 six-variable linear equations. A least squares solution of the system of equations was found to obtain a fitting parameter $\alpha_j$(j=0, 1, ..., 5). The fitting parameter $\alpha_j$ was substitute into a quintic polynomial to obtain the smoothed spectra $B'_i$, $P'_i$, $M'_i$ of the three types of samples.

C) Baseline correction of Raman spectra. For each smoothed spectral signal, an adaptive iterative reweighted penalized least squares method was adopted for baseline correction. A curve roughness penalty coefficient λ=100 was set to obtain the spectra $B''_i$, $P''_i$, $M''_i$ after baseline correction.

D) Determination of a range of characteristic peaks of Raman spectra. 20 spectra were extracted from each of $B''_i$, $P''_i$, $M''_i$ to form a training set $C_{i1}$(i1=1, 2, ..., 60). Principal component analysis was performed on $C_{i1}$ to extract the first two principal components $PC_1$ and $PC_2$.

Figure 3:
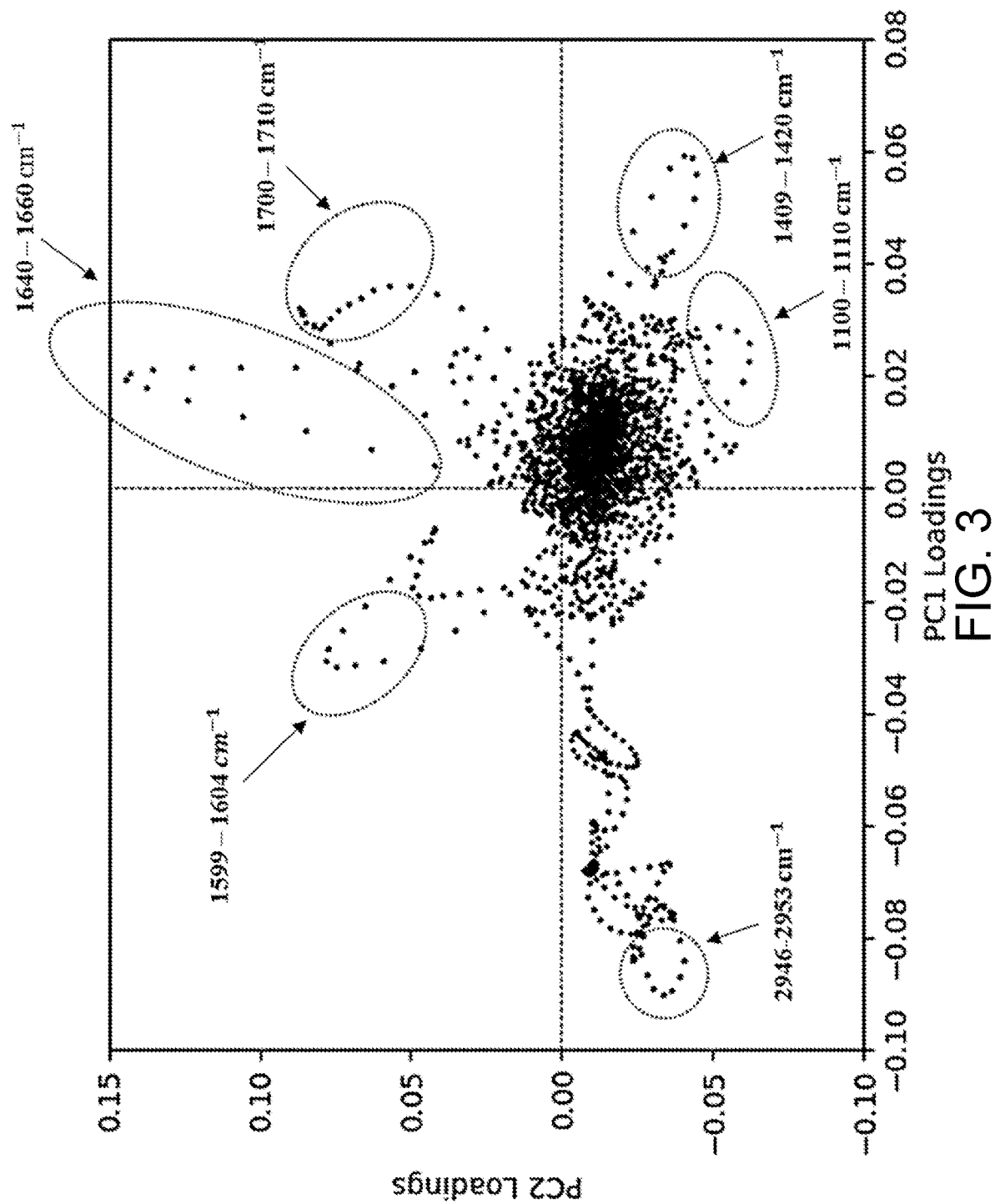
FIG. 3 is a principal component loading scatter plot according to the disclosure.

A two-dimensional coordinate graph was established with a load coefficient $\alpha_{1k}$ as the horizontal axis and a load coefficient $\alpha_{2k}$ as the vertical axis. The load coefficient $\alpha_{1k}$ and the load coefficient $\alpha_{2k}$ corresponding to $\beta_k$ of the same wave band in the two principal components were taken as scatter coordinates ($\alpha_{1k}$, $\alpha_{2k}$), which were drawn in the two-dimensional coordinate graph to form a principal component loading scatter plot, as shown in FIG. 3.

Figure 4:
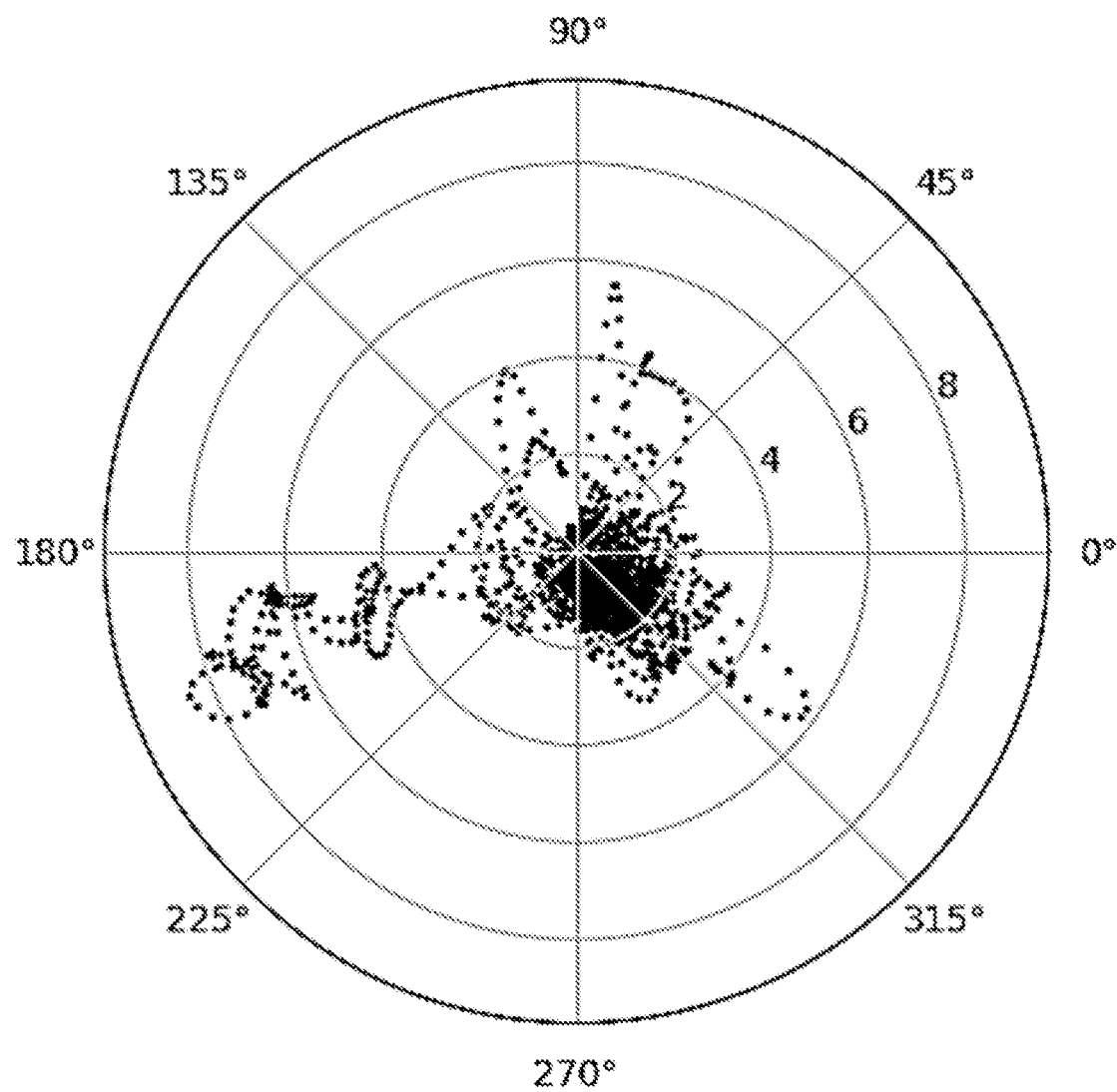
FIG. 4 is a principal component loading scatter plot based on polar coordinates according to the disclosure.

The Cartesian coordinates ($\alpha_{1k}$, $\alpha_{2k}$) were converted into polar coordinates ($d_k$, $\theta_k$), that is, the principal component loading scatter plot was divided into eight sector-shaped regions according to angles with the coordinate center of the plot as the origin. The result is shown in FIG. 4.

E) Extraction of Raman Characteristic Peaks.

For each region $D_i$, a weighted distance $d_{ik}$ of each scatter ($\alpha_{ik}$, $\alpha_{2k}$) from the coordinate center was calculated. Then, a variance $v_i$ and a mean $e_i$ were calculated according to the weighted distances $d_{ik}$ of all scattered points in each region. The maximum weighted distance $d_{ik}$ was taken as the maximum polar diameter $r_i$, and judgment was then performed. For each maximum polar diameter $r_i$, if $$\frac{r_i - e_i}{v_i} \geq 3$$

was satisfied, the Raman shift point $\beta_k$ corresponding to the maximum polar diameter $r_i$ was regarded as a Raman characteristic peak.

In the example, 5 filtered characteristic peaks were 1605 cm$^{-1}$, 1646 cm$^{-1}$, 1416 cm$^{-1}$, 1708 cm$^{-1}$, and 2952 cm$^{-1}$.

F) Establishment of a classification model of pork and beef based on Raman spectra. A training set and a test set were divided by adopting a 10-fold cross-validation method 10 times.

The training set and the test set were divided by adopting the 10-fold cross-validation method 10 times. A stratified sampling method was adopted, so that each mutually exclusive subset has 3 beef and pork samples each.

Peak intensities corresponding to the five Raman characteristic peaks extracted in the above step and combined with category labels were inputted into a classifier for training. A k-nearest neighbor classifier was adopted for the classifier. A value range nearest to the actual number k in the classifier was 4~10. A model was established for different k values of the k-nearest neighbor classifier. The model with the maximum separation weighted result F1 score was taken as the final classification model. The final classification model was used to classify and identify the meat samples to be detected.

In the model selected in the example, k=5, and the classification result is shown in Table 1.

TABLE 1

| | Classification result | | |
|---|---|---|---|
| | Predicted result | | |
| Actual condition | Pork | Beef | Adulteration (50%) |
| Pork | 30 | 0 | 0 |
| Beef | 0 | 30 | 0 |
| Adulteration (50%) | 0 | 0 | 30 |

It can be seen from the above table that the classification model adopting the five Raman characteristic peaks extracted by the method as input parameters can accurately distinguish the beef, pork, and adulterated meat samples. It shows that the characteristic extraction method has high accuracy, and the number of extracted characteristics is small, which effectively simplifies the model and speeds up the speed of the classification algorithm.

What is claimed is:

1. A method for extracting Raman characteristic peaks employing improved principal component analysis, comprising:
   1) Using a confocal microscopic Raman-spectroscopic instrument to collect Raman spectroscopic data from surfaces of pork and beef samples;
   2) Performing preprocessing on the Raman spectroscopic data, then performing principal component analysis, then establishing a principal component loading scatter plot, then analyzing and extracting scatter characteristics of the principal component loading scatter plot, and filtering the Raman characteristic peaks according to the scatter characteristics, the step 2) comprising:
      2.1) for a Raman spectrum dataset $B(B_1, B_2, \ldots, B_n)$ of n samples and m wave bands obtained after the preprocessing, that is, each spectrum $B_i$ containing m wave bands, adopting a random sampling method to extract ⅔ spectrum from the dataset B to form a training set $C(C_1, C_2, \ldots, C_{2n/3})$, then performing the principal component analysis on the training set C to extract first two principal components_$PC_1$_and_$PC_2$ expressed as:

$$PC_1 = \sum_{k=1}^{m} \alpha_{1k} \beta_k$$

$$PC_2 = \sum_{k=1}^{m} \alpha_{2k} \beta_k$$

where $\beta_k$ is a k-th wave band, $\alpha_{1k}$ represents a load factor corresponding to the k-th wave band under the first principal component, and_$\alpha_{2k}$ represents a load factor corresponding to the k-th wave band under the second principal component;

2.2) drawing a load distribution diagram in a form of polar coordinates establishing a two-dimensional coordinate graph with a load coefficient $\alpha_{1k}$ as a horizontal axis and a load coefficient $\alpha_{2k}$ as a vertical axis, taking the load coefficient $\alpha_{1k}$ and the load coefficient $\alpha_{2k}$ corresponding to a Raman shift point $\beta_k$ of a same wave band in the two principal components as scatter coordinates ($\alpha_{1k}$, $\alpha_{2k}$) drawn in the two-dimensional coordinate graph to form the principal component loading scatter; then converting scatters from Cartesian coordinates ($\alpha_{1k}$, $\alpha_{2k}$) into polar coordinates ($d_k$, $\theta_k$), and dividing, according to angles of the polar coordinates, a wavelength range occupied by all scatters into eight regions $D_i(i=1, 2, \ldots, 8)$ respectively being $$\left[0, \frac{\pi}{4}\right), \left[\frac{\pi}{4}, \frac{\pi}{2}\right), \left[\frac{\pi}{2}, \frac{3\pi}{4}\right), \left[\frac{3\pi}{4}, \pi\right), \left[\pi, \frac{5\pi}{4}\right), \left[\frac{5\pi}{4}, \frac{3\pi}{2}\right), \left[\frac{3\pi}{2}, \frac{7\pi}{4}\right), \left[\frac{7\pi}{4}, 2\pi\right);$$

2.3) determining positions of characteristic peaks for each region $D_i$, calculating a weighted distance $d_{ik}$ of each scatter ($\alpha_{1k}$, $\alpha_{2k}$) from a coordinate center;

$$d_{ik} = \frac{\sqrt{(\lambda_1 \alpha_{1k})^2 + (\lambda_2 \alpha_{2k})^2}}{\sqrt{\lambda_1^2 + \lambda_2^2}}$$

where $\lambda_1$ and $\lambda_2$ respectively represent weights of the first principal component and the second principal component, and $d_{ik}$ represents a weighted distance of a scatter corresponding to the k-th wave band of an i-th region $D_i$;

then calculating a variance $v_i$ and a mean $e_i$ of the weighted distances $d_{ik}$ of all scattered points in each region, taking a maximum weighted distance $d_{ik}$ as a maximum polar diameter $r_i$ to then perform a following judgment, wherein for each maximum polar diameter $r_i$, if $$\frac{r_i - e_i}{v_i} \geq 3$$

is satisfied, the Raman shift point $\beta_k$ corresponding to the maximum polar diameter $r_i$ is regarded as a Raman characteristic peak.

2. The method for extracting Raman characteristic peaks employing improved principal component analysis according to claim 1, wherein the scatter characteristics are a polar diameter and a polar angle of a scatter.

3. The method for extracting Raman characteristic peaks employing improved principal component analysis according to claim 1, wherein the preprocessing comprises sequentially performing smoothing and baseline correction processing.

4. The method for extracting Raman characteristic peaks employing improved principal component analysis according to claim 1, wherein dividing the wavelength range occupied by all scatters into eight regions according to the angles of the polar coordinates comprises dividing the principal component loading scatter plot into eight sector-shaped regions according to the angles with the coordinate center of the plot as an origin.

\* \* \* \* \*